United States Patent [19]

Sullivan et al.

[11] Patent Number: 4,770,806
[45] Date of Patent: Sep. 13, 1988

[54] DEODORIZED COMPOSITIONS

[75] Inventors: Alfred B. Sullivan, Wadsworth; Raleigh W. Wise, Akron, both of Ohio

[73] Assignee: Monsanto Company, St. Louis, Mo.

[21] Appl. No.: 502,880

[22] Filed: Jun. 9, 1983

[51] Int. Cl.$^4$ .................. C08K 5/44; C08K 5/47; C08L 21/00; C01B 31/08

[52] U.S. Cl. .................. 252/182.17; 252/189; 502/416; 260/708

[58] Field of Search ............ 252/182, 189; 502/416; 260/708

[56] References Cited

U.S. PATENT DOCUMENTS

| | | | |
|---|---|---|---|
| 1,511,984 | 10/1924 | Spear | 524/215 |
| 2,067,985 | 5/1933 | Sargent | 252/3 |
| 2,120,227 | 6/1938 | Brant | 260/156.5 |
| 2,382,813 | 8/1945 | Paul | 260/795 |
| 2,725,360 | 11/1955 | Lewis et al. | 252/445 |
| 2,768,988 | 10/1956 | Cristensen | 260/786 |
| 3,118,844 | 1/1964 | Forrester et al. | 252/313 |
| 3,798,877 | 3/1974 | Lamb | 260/708 X |
| 3,823,161 | 7/1974 | Lesser | 260/332.2 |
| 4,035,336 | 7/1977 | Jordan et al. | 260/42.47 |
| 4,035,449 | 7/1977 | Zakaryan | 260/972 |
| 4,212,852 | 7/1980 | Aibe et al. | 423/230 |
| 4,336,103 | 12/1982 | Pearce et al. | 260/967 |

FOREIGN PATENT DOCUMENTS 0080861  6/1983  European Pat. Off. .

OTHER PUBLICATIONS

Chem. Abst. 95, 12055 (1981), Deodorant for Malodorous Sulfur Compounds, Jpn. Kokai Tokkyo Koho, 81-05,133, Jan. 20, 1981.
Hackh's Chemical Dictionary, 4th ed., New York, McGraw-Hill Book Co., 1969, p. 15.
The Condensed Chemical Dictionary, 10th ed., New York, Van Nostrand Reinhold Co., 1981, pp. 194–195 and 322.

*Primary Examiner*—John F. Terapane
*Assistant Examiner*—Virginia B. Caress
*Attorney, Agent, or Firm*—Gordon B. Seward; Larry R. Swaney

[57] ABSTRACT

Deodorized compositions are described comprising an intimate mixture of a malodorous sulfur containing compound and activated carbon.

20 Claims, No Drawings

DEODORIZED COMPOSITIONS

This application relates to deodorized compositions, and more partioularly, to deodorized compositions comprising admixtures of malodorous solid compounds and activated carbon.

BACKGROUND OF THE INVENTION

Many sulfur containing solid compounds exhibit potentially useful properties but for their obnoxious and unpleasant odors which prevent their use in applications where they are exposed to the atmosphere. The source of the unpleasant odor varies from product to product and sometimes is unknown, but is generally due to impurities, or due to by-products formed during the preparation of the major product, or due to decomposition of the product during storage or use. Often, purification by conventional techniques does not eliminate the objectionable odor or is too expensive to be practicable. The failure to eliminate odors by purification techniques is because the offensive material is usually present in extremely small amounts and because of the ability of the human nose to detect the presence of odorous materials at concentrations of parts per million, and in some instances, at concentrations of parts per billion. The problem is particularly severe for compounds derived from low molecular weight sulfur compounds. Accordingly, the use of malodorous sulfur solid compounds could be greatly expanded if an inexpensive solution to the odor problem could be found.

SUMMARY OF THE INVENTION

In accordance to this invention, it has been found that an odorless or essentially odorless particulate composition comprising a malodorous particulate compound is obtained by intimately mixing therewith a deodorizing amount of activated carbon. Surprisingly, the malodor is eliminated with relatively small quantities of activated carbon without treating a solution of a malodorous solid material, without passing a sweeping gas through the malodorous solid material, and without separating the activated carbon from the mixture. The quantity of activated carbon in the mixture is so small that there is no significant deleterious effect upon the deodorized composition.

The amount of activated carbon needed varies depending upon a number of factors, such as, the adsorption capacity of the activated carbon, activated carbon particle size, and the amount of the malodorous material present in the specimen to be deodorized. Lesser quantities of activated carbon are needed with a high adsorption carbon (as indicated by larger iodine number) or with lower particle size carbon, whereas, larger quantities are needed to deodorize specimens containing high levels of malodorous material. Generally, twenty weight percent, preferably, 1-10 weight percent, and more preferably, 2-6 weight percent, of activated carbon is sufficient to effect deodorization. Sometimes 0.5 parts by weight of activated carbon per 100 parts by weight of the malodorous composition (0.5 weight percent) is sufficient to reduce or totally eliminate the malodor. The amount of activated carbon needed for any particular malodorous material is readily determined by increasing the amount of activated carbon until the malodor disappears.

Both the activated carbon and the malodorous particulate particulate compound are in particulate form, for example, 20 mesh (about 0.83 mm) or below. Preferably, both the particulate compound and the activated carbon pass through a 100 mesh seive (about 0.15 mm). The two solids may be blended by any known method such as by tumbling, stirring, or fluidization. For best results, the activated carbon should be fairly uniformly dispersed throughout the material to be deodorized. It is advantageous that the average particle size of the activated carbon is equal to or less than the average particle size of the malodorous organic compound.

Activated carbon, useful in the practice of this invention, is a form of carbon which is microcrystalline, nongraphitic carbon having high internal porosity and a specific surface area of at least 300 $m^2/g$, preferably 500–2000 $m^2/g$, and more preferably 1000–2500 $m^2/g$. Surface areas are determined by the nitrogen BET method. The activated carbon can be in powdered or granular form, but powdered activated carbon is preferred. However, the activated carbon particulate size must be small enough so that it remains evenly distributed throughout the composition. Therefore, granular activated carbon is less effective or ineffective particularly if the granules settle to the bottom of the composition. The limiting particle size cannot be ascertained with absolute certainty because it varies depending upon the particle size of malodorous material and the amount of activated carbon present. Granular activated carbon efficiency can be improved by grinding it to a powder either prior to or upon mixing with the malodorous material. Generally, powdered activated carbon with a particle size of 50 mesh (about 0.30 mm) U.S. Standard Seive is satisfactory but generally larger amounts are required to achieve the same level of deodorization obtained by smaller particle size activated carbon. Thus, activated carbon with a particle size of 100 mesh (about 0.15 mm) or below is more satisfactory. A particle size of 200 mesh (about 75 microns) is preferred. More preferably, 90% or more of the activated carbon has a particle size of 325 mesh (about 42 microns) or below. Satisfactory activated carbons exhibit an adsorption capacity of about 20–85% $CCl_4$ as determined by ASTM D-3467 or iodine numbers of about 500 to 1200, preferably 800 or above. As indicated by the high surface area, activated carbon is characterized by high porosity; activated carbon having pores 3 mm and less are preferred since they exhibit high adsorptive capacity per unit volume and high retentive capacity. This means that activated carbon with larger pores may be used, but larger quantities may be required to be effective. Activated carbon should not be confused with carbon black, furnace black, channel black and the like, which are reinforcing fillers or pigments of low porosity and low surface area. For details on activated carbon, refer to *Kirk-Othmer, Encyclopedia of Chemical Technology, Third Edition, Volume 4*, pages 561–569, which disclosure is incorporated herein by reference. Activated carbon suitable in the practice of the invention is commercially available from a number of United States companies, ibid, p. 563.

The invention is useful in deodorizing malodorous particulate compositions comprising a malodorous particulate organic compound having sulfur in the molecule and particularly which have sulfur in combination with carbon, nitrogen, phosphorous and oxygen moieties. Many compounds of this type are herbicides, pesticides, or rubber additives such as vulcanizing agents, accelerators and prevulcanization inhibitors. The invention is particularly effective for deodorizing malodorous particulate organic compounds containing at least one (and up to six or more) $C_1$-$C_4$ alkylthio radicals or said radical substituted by phenyl. Compounds containing primary and secondary alkylthio radicals are often especially malodorous. It should be understood, of course, that the compounds themselves in pure form may not necessarily be malodorous but that such compounds as normally manufactured or used do exhibit foul odors because of impurities, decomposition products or by-products produced during manufacture. In any event, essentially odorless compositions are obtained by the practice of this invention.

Examples of said thio radicals are methylthio, ethylthio, propylthio, butylthio, isopropylthio, sec-butylthio, isobutylthio, tert-butylthio, benzylthio, α-methyl benzylthio, and α,α-dimethyl benzylthio.

Examples of solid compounds, melting above room temperature, preferably above 50° C., improved by the invention are sulfenamides, sulfenimides, sulfinamides, sulfonamides, dithiocarbamates, thiocarbamates, thiolcarbamates, methylene thioethers, phosphorothioates, phosphorodithioates, phosphonothioates, and phosphonodithioates. Examples of such solid particulate compounds are described in the following U.S. Pat. Nos.: 4,380,609; 4,342,705; 4,156,680; 4,165,310; 3,872,061; 3,705,135; 3,692,770; 4,311,648; 3,849,418; 3,686,169; 3,586,696; 3,546,185; 3,539,538; 4,018,855; 3,933,907; and 3,855,261. A preferred subclass of rubber additives are particulate sulfenamides described in U.S. Pat. Nos. 4,380,609; 3,586,696 and 3,933,907.

Illustrative examples of satisfactory compounds are N,N,N',N',N'',N''-hexakis (isopropylthio)-1,3,5-triazine-2,4,6-triamine; N,N,N',N',N'',N''-hexakis (methylthio)-1,3,5-triazine-2,4,6-triamine, N,N,N',N'-tetra(isopropylthio) 6-chloro-1,3,5-triazine-2,4-diamine, N-(isopropylthio)phthalimide; N-(benzylthio)phthalimide; N-(t-butylthio)phthalimide; N-(n-butylthio)phthalimide; N-(sec-butylthio)phthalimide; N-(n-propylthio)phthalimide; N-(isobutylthio)phthalimide; N-(methylthio)phthalimide; N-(ethylthio)phthalimide; α-acetyl-α,α-di(isopropylthio)acetanilide; α-acetyl-α,α-di(methylthio)acetanilide; α-acetyl-α,α-di(ethylthio)-acetanilide; α-acetyl-α,α-di(propylthio)acetanilide; α-acetyl-α,α-di(butylthio)acetanilide; α-benzoyl-α,α-di(isopropylthio)acetanilide; 2,2-di(isopropylthio)-1,3-cyclohexanedione; 2,2-di(isopropylthio)2-cyanoacetamide; 2,2-di(isopropylthio)-2-cyanoacetanilide; N-(isopropylthio)-2(2H)hexahydroazepinone; 2-(t-butyldithio)benzothiazole; 2(isopropyldithio)-benzothiazole; 2-(ethyldithio)benzothiazole; 2(methyldithio)benzothiazole; 1,4-di(isopropylthio)-2,5-piperazinedione; N-(benzylthio)succinimide; 2-(isopropyldithio)benzimidazole; (isopropylthio)phenylcarbamic acid, phenyl ester; bis(isopropylthio)phenylcarbamic acid, 1,3-phenylene ester; N-isopropylthio-N-phenylmethacrylamide; N,N'-bis(isopropylthio)oxanilide; N,N'-bis(methylthio)oxanilide; N,N',N''-tris(isopropylthio)-N,N',N''-tricyclohexyl phosphorothioic triamide; N,N',N''-tris(isopropylthio)-N,N',N''-tribenzyl phosphorothioic triamide, N,N',N''-tris(isopropylthio)phosphoric acid trianilide; N,N'-bis(isopropylthio)-N,N'-diphenyl-p-tolylphosphoric diamine; N-isopropylthio-N,P,P-triphenylphosphinic amide; N,N',N''-tris(n-butyl)-N,N',N''-triphenyl phosphoric triamide; N,N'-diphenyl-N,N'-bis-(isopropylthio)phosphorodiamine; N-isopropyl-N'-isopropylthio-2-benzothiazole sulfonamide, and N-cyclohexyl-N'-propylthio-2-benzothiazole sulfonamide.

DESCRIPTION OF THE PREFERRED EMBODIMENTS

To illustrate the invention, samples are prepared by placing in a 30 ml. bottle one gram of a malodorous particulate compound and 40 mg. of powdered activated carbon. The sample is stirred with a spatula until the activated carbon is uniformly distributed throughout the composition as indicated by the homogeneous appearance and color of the sample. Control samples are prepared by placing in a 30 ml. bottle one gram of the identical malodorous particulate compound, but leaving out the activated carbon. The bottles are then capped and stored overnight. The samples are then submitted to an odor panel comprising six individuals. The panelists are instructed to uncap the bottles, to smell the samples, and to rate the degree of odor by assigning the values of "0" for no odor, "2" for a slight odor, "5" for a moderate odor, "8" for a high odor, and "10" for an extreme odor. A value of 2 is regarded as being the threshold level that an individual panelist could detect odor, whereas, higher values are regarded as being more subjective and subject to greater variation among panelists. The samples are capped and allowe to stand at least 30 minutes before submission to another panelist.

The activated carbon used in Table 1 is Nuchar® SA powdered activated carbon manufactured by Westvaco Company. Typical properties include surface area of 1400-1800 $m^2$/g (Nitrogen BET method), total pore volume of 2.2-2.5 $cm^3$/g, iodine number of 900 mg/g min., and U.S. Seive Analysis of thru 100 mesh (95-100%), thru 200 mesh (85-95%) and thru 325 mesh (65-85%).

The results are tabulated in Table 1. In the table, controls are designated by the letter "A", and samples containing 4 weight percent of activated carbon by the letter "B". The odor ratings are the numerical average of the values assigned by the six panelists.

The data in Table 1 show that 4 weight percent of powdered activated carbon eliminates odor or reduced odor to acceptable levels. Concentration studies (not shown) indicate that in samples still having odor, the odor can be eliminated or reduced further by increasing the amount of activated carbon, for example to 10 weight percent. The studies also indicate that reduction or elimination of odor in some samples can be achieved with as little as one weight percent of activated carbon.

Compositions of the invention prepared with a different powdered activated carbon, Nuchar Aqua PAC®, are illustrated in Table 2. This activated carbon is characterized by an iodine number of 600 mg/g min., and U.S. Seive Analysis of thru 100 mesh (99% min.), thru 200 mesh (97% min.) and thru 325 mesh (90% min.). The samples are prepared and odor ratings are determined as in Table 1. Samples, designated by the letter "A", are controls containing no additives.

TABLE 1

| | COMPOUND | M.P. °C. | ODOR RATING A | B |
|---|---|---|---|---|
| EXAMPLE 1 | N,N',N''—tris(isopropylthio)phosphoric acid | 120-121 | 7.3 | 0.3 |

TABLE 1-continued

|  | COMPOUND | M.P. °C. | ODOR RATING A | B |
|---|---|---|---|---|
|  | trianilide |  |  |  |
| EXAMPLE 2 | (Isopropylthio)phenylcarbamic acid, methyl ester | 52-53 | 5.3 | 2.8 |
| EXAMPLE 3 | N—(sec-butylthio)phthalimide | 49 | 7.7 | 2.0 |
| EXAMPLE 4 | N—(benzylthio)phthalimide | 157-161 | 3.5 | 0.7 |
| EXAMPLE 5 | N—(t-butylthio)succinimide | 157 | 8.0 | 2.2 |
| EXAMPLE 6 | Hexakis(isopropylthio)-1,3,5-triazine-2,4,6-triamine | 151-152 | 5.0 | 0 |
| EXAMPLE 7 | N—(isopropylthio)phthalimide | 67-70 | 7.3 | 2.0 |
| EXAMPLE 8 | N,N'—di(isopropylthio)oxanilide | 139-141 | 3.0 | 0.3 |
| EXAMPLE 9 | Bis(phenylcarbamoyl)bis(propylthio)methane | 123-124 | 7.2 | 0 |
| EXAMPLE 10 | α-Acetyl-α,α-di(isopropylthio)acetanilide | 118-119 | 2.3 | 0.3 |
| EXAMPLE 11 | N,N',N"—tris(isopropylthio)phosphoric acid trianilide (15% on $CaCO_3$, Sumitard-XL) | — | 6.5 | 0.7 |
| EXAMPLE 12 | N—cyclohexyl-N'—isopropylthio-2-benzothiazole sulfonamide (Santarder APR) | 105 min. | 4.5 | 0.3 |
| EXAMPLE 13 | N—(n-butylthio-phthalimide) | 62-64 | 8.5 | 2.5 |

Samples, designated by the letter "B", contain 4 weight percent of activated carbon. The sample, designated by the letter "C", contains 1 g. of the malodorous chemical compound and 2 g. of aluminum silicate, Zeolex 23. The sample, designated by the letter "D", is the same as "C", but in addition contains 40 mg. of activated carbon (4 weight percent based on the chemical compound). Example 14 is a compound as prepared without purification (crude) which is especially malodorous. The result are shown in Table 2. The data indicate that 4 weight percent of activated carbon substantially reduces odor but that in Example 16 more activated carbon is needed. Sample C of Example 14 shows that dilution by addition of 200 percent by weight of an inert particulate aluminum silicate results in a reduction of odor but not to an acceptable level. Sample D of Example 14 shows that 4 weight percent of activated carbon eliminates the odor completely.

The effect of granular and powdered activated carbon is illustrated by preparing samples with granular activated carbon and samples with the same granular activated carbon after grinding to powdered form by use of a mortar and estle. The malodorous material is crude hexakis(isopropylthio)-1,3,5-triazine 2,4,6-triamine, odor rating 9.7. The granular activated carbon has a particle size of 6 x 12, U.S. screen and an adsorption capacity of 60% carbon tetrachloride, ASTM D-3802, Barnebey-Cheney Type AC.

TABLE 2

|  | COMPOUND | M.P. °C. | ODOR RATING A | B | C | D |
|---|---|---|---|---|---|---|
| EXAMPLE 14 | Hexakis(isopropylthio)-1,3,5-triazine-2,4,6-triamine | 129-135 (crude) | 9.7 | 2.2 | 6.8 | 0.0 |
| EXAMPLE 15 | α-Acetyl-α,α-di(methylthio)-acetanilide | 114-115 | 2.3 | 0.3 |  |  |
| EXAMPLE 16 | N-(t-butylthio)formanilide | 52-52.5 | 5.5 | 3.0 |  |  |

The particle size of the activated carbon after grinding was not determined but appeared to be 80 mesh (about 0.18 mm) or below. Samples are prepared by blending 10 weight percent of either the granular or powdered activated carbon into the malodorous material. Odor ratings are determined by an odor panel as described above. The sample containing the granular activated carbon has an odor rating of 7.0, whereas, the sample containing the powdered activated carbon has an odor rating of 2.0.

Although the invention has been illustrated by typical examples, it is not limited thereto. Changes and modifications of the examples of the invention herein chosen for purposes of disclosure can be made which do not constitute departure from the spirit and scope of the invention.

We claim:

1. An essentially odorless particulate composition comprising an intimate mixture of a malodorous, solid, particulate organic compound containing at least one $C_1$–$C_4$ alkylthio radical or said radical substituted by phenyl and, in an amount sufficient to deodorize said malodorous compound, activated carbon having a surface area of at least 300 square meters per gram wherein said malodorous compound is a rubber additive.

2. The composition of claim 1 comprising powdered activated carbon having a surface area of about 500-2500 square meters per gram.

3. The composition of claim 2 in which the particle size of both the organic compound and the activated carbon is 100 mesh or below.

4. The composition of claim 3 in which the activated carbon is twenty weight percent or less of the composition.

5. The composition of claim 4 in which the activated carbon is 1-10 weight percent of the composition.

6. The composition of claim 5 in which 90% or more of the activated carbon has a particle size of 325 mesh or below.

7. The composition of claim 5 in which the average particle size of the activated carbon is equal to or less than the average particle size of the malodorous organic compound.

8. The composition of claim 7 in which the rubber additive is a sulfenamide derived from an amine, amide, or imide.

9. The composition of claim 8 in which the rubber additive is N-($C_1$–$C_4$ alkylthio)phthalimide.

10. The composition of claim 9 in which the rubber additive is N-(isopropylthio)phthalimide.

11. The composition of claim 8 in which the rubber additive is a $C_1$–$C_4$ alkyl sulfenamide derived from 1,3,5-triazine-2,4,6-triamine.

12. The composition of claim 11 in which the rubber additive is hexakis(isopropylthio)-1,3,5-triazine-2,4,6-triamine.

13. The composition of claim 8 in which the rubber additive is a $C_1$–$C_4$ sulfenamide derived from oxamide or oxanilide.

14. The composition of claim 13 in which the rubber additive is N,N'-di(isopropylthio)oxanilide.

15. The composition of claim 8 in which the rubber additive is N,N',N''-tri(isopropylthio)phosphoryl trianilide.

16. An essentially odorless particulate composition consisting essentially of an intimate mixture of a malodorous particulate organic compound melting above 50° C. and containing at least one $C_1$–$C_4$ alkylthio radical and, in an amount of 1 to 10 weight percent of the composition, powdered activated carbon having a surface area of about 500–2500 square meters per gram.

17. The composition of claim 16 in which the activated carbon has an iodine number of 800 or more.

18. The composition of claim 17 in which the particle size of both the organic compound and activated carbon is 100 mesh or below.

19. The composition of claim 18 in which at least 90% of the activated carbon has a particle size of 325 mesh or below.

20. The composition of claim 18 in which the malodorous particulate compound is hexakis(isopropylthio)-1,3,5-triazine-2,4,6-triamine.

* * * * *